United States Patent
Randall

(10) Patent No.: US 8,663,269 B2
(45) Date of Patent: Mar. 4, 2014

(54) PIVOT TIPPED ROD FORCEPS

(75) Inventor: Peter Randall, Middleboro, MA (US)

(73) Assignee: Holmed Corporation, South Easton, MA (US)

( * ) Notice: Subject to any disclaimer, the term of this patent is extended or adjusted under 35 U.S.C. 154(b) by 1583 days.

(21) Appl. No.: 11/526,526

(22) Filed: Sep. 25, 2006

(65) Prior Publication Data

US 2007/0239204 A1    Oct. 11, 2007

Related U.S. Application Data

(60) Provisional application No. 60/721,773, filed on Sep. 29, 2005.

(51) Int. Cl.
*A61B 17/00* (2006.01)

(52) U.S. Cl.
USPC .......................................................... 606/207

(58) Field of Classification Search
USPC ............. 606/205, 207, 208; 81/300, 427, 424
See application file for complete search history.

(56) References Cited

U.S. PATENT DOCUMENTS

| | | | | |
|---|---|---|---|---|
| 31,882 A * | 4/1861 | Bruhl | .................................. | 68/88 |
| 2,109,147 A * | 2/1938 | Grosso | ........................... | 606/205 |
| 2,507,710 A * | 5/1950 | Grosso | ........................... | 606/205 |
| 3,742,957 A * | 7/1973 | White | ............................ | 606/208 |
| 3,866,324 A | 2/1975 | Walser | | |
| 5,047,046 A | 9/1991 | Bodoia | | |
| 5,752,973 A * | 5/1998 | Kieturakis | ..................... | 606/207 |
| 5,891,161 A * | 4/1999 | Graser | ........................... | 606/148 |
| 5,911,736 A * | 6/1999 | Dingler et al. | ................ | 606/208 |
| 6,716,218 B2 * | 4/2004 | Holmes et al. | ................ | 606/105 |
| 7,871,424 B2 | 1/2011 | Abdelgany | | |
| 2004/0089117 A1* | 5/2004 | Hsien | .............................. | 81/424 |
| 2004/0111113 A1 | 6/2004 | Nakamura et al. | | |
| 2004/0231472 A1* | 11/2004 | Lin | ............................... | 81/177.8 |
| 2005/0070955 A1 | 3/2005 | Young | | |
| 2006/0230886 A1* | 10/2006 | Hsien | .............................. | 81/424 |
| 2006/0265003 A1 | 11/2006 | Abdelgany | | |
| 2009/0024123 A1 | 1/2009 | Young | | |

\* cited by examiner

*Primary Examiner* — Gary Jackson
*Assistant Examiner* — Michael Mendoza
(74) *Attorney, Agent, or Firm* — Cesari and McKenna, LLP

(57) ABSTRACT

A pivot tipped rod forceps instrument for surgical procedures is provided. The rod forceps has handle members attached at a pin. A pivoting jaw assembly having a pivoting tip is disposed at a distal end of each handle member. The pivoting jaw assembly is opened to receive a surgical rod or other object to be placed by the surgeon. The jaw assembly is then closed to engage the object. The pivoting tips are contoured to tightly engage the surgical rod. Once the rod is held by the tips, the whole pivoting jaw assembly can be rotated to a desired angle to aid the surgeon in manipulating the rod or other item as desired.

17 Claims, 2 Drawing Sheets

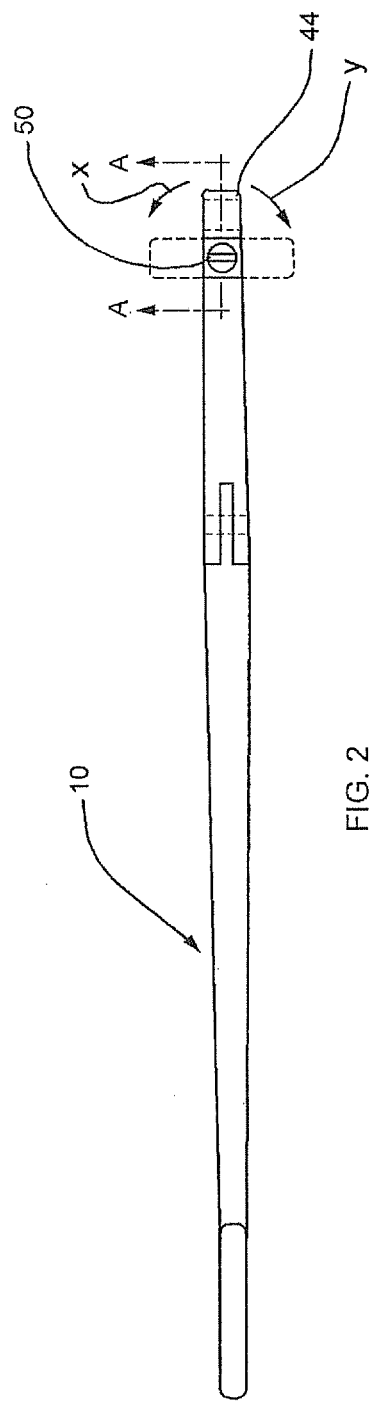
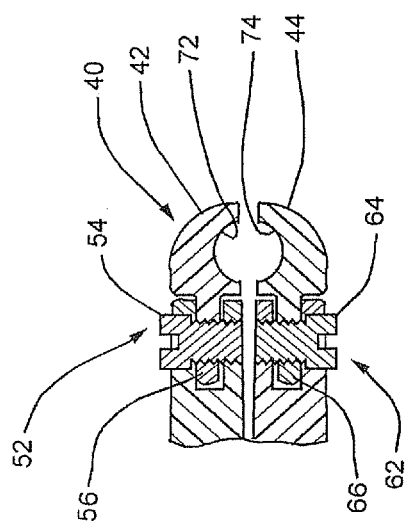
FIG. 2
FIG. 3

US 8,663,269 B2

PIVOT TIPPED ROD FORCEPS

CROSS-REFERENCE TO RELATED APPLICATIONS

The present application claims the benefit of U.S. Provisional Patent Application Ser. No. 60/721,773, which was filed on Sep. 29, 2005, by Holmes for a PIVOT TIPPED ROD FORCEPS, which and is hereby incorporated by reference.

BACKGROUND OF THE INVENTION

1. Field of the Invention

This invention relates generally to surgical instrumentation, and more particularly, to instrumentation for use in spinal surgery and other surgery.

2. Background Information

Various medical instruments and appliances are used in the treatment of spinal column deformities and injuries. In certain medical circumstances, it is necessary to place a mechanical device, such as a stabilization rod, adjacent to the spine. This is to promote the natural healing of the spine in a straight spatial disposition, or to enhance straightening of the spine in cases of disease such as scoliosis. In some surgical procedures, chips of bone which have been removed from another portion of the body, such as the hip, are placed in proximity to the healing spinal site. These chips act as mortar to promote bone fusion.

The spinal rods are placed along the spinal column and various fixation appliances are mounted along the rods to maintain the rods in the desired position and orientation. Implants are pushed up and down the rods such as hooks. Rod holders may be used as a stop. While a surgeon is mounting the rods, rod hooks and various other components, the surgeon pushes items along the rod and may either distract bone by pulling it away from the work site or must compress bone to pull it together if broken, for example. A standard distracter/compressor is used to accomplish these and many other actions during spinal surgery.

Pressure is thus applied from some distance in order to move implants along a rod or to distract or compress a rod in place or to distract bone or implants into the most favorable position. The positioning is important in order to fix the correct position of the rods and the implants while providing the surgeon the best visualization of the work site.

Prior instruments required the surgeon or a member of the surgical team to hold a distracter directly at the desired angle, however, the distracter instrument itself may, in such a case obstruct the surgeon's view of the work site. It has been known to provide an instrument with a bend in it, to allow a better view, but the bend may not allow the most leverage when a good deal of force is required. Detachable tips have also been used, which detachable tips are placed on the end of a standard distracter allowing distraction or compression at a particular angle which allows the instrument to be rotated out of the surgeon's view yet still applying pressure at the correct position on the rod or bone. Ratcheted tips have also been described as in U.S. Pat. No. 6,716,218, which issued on Apr. 6, 2004, for an INSTRUMENT FOR BONE DISTRACTION AND COMPRESSION HAVING RATCHETING TIPS, which is incorporated by reference herein. However, there are certain instances in which a different angle is required by the surgeon for a particular surgical procedure.

SUMMARY OF THE INVENTION

The disadvantages of the prior techniques are overcome by the present invention which provides pivot tipped rod forceps. The rod forceps have handle members attached at a pin. A pivoting tip is disposed at a distal end of each handle member. The pivoting tips are formed to engage a surgical rod. Once the rod is in place within the tips, the whole end assembly can be rotated to a desired angle to aid the surgeon in manipulating the rod or other item as desired.

An advantage is gained by this arrangement in that the rod may be aligned parallel with the basic instrument, allowing the rod to pass through a much smaller incision, or in some cases, the rod passes through tubes or port devices. Once through the facia, pressure may be exerted in a downward manner on the end of the rod, and the rotating tips allow the rod to pivot down into the seats of the pedicle screws already in place.

BRIEF DESCRIPTION OF THE DRAWINGS

The invention description below refers to the accompanying drawings, of which:

FIG. 2 is a schematic side elevation of an illustrative embodiment of the rod forceps of the present invention; and FIG. 3 is an exploded cross section of the pivoting tips of an illustrative embodiment of the rod forceps of the present invention taken along lines A-A of FIG. 2.

DETAILED DESCRIPTION OF AN ILLUSTRATIVE EMBODIMENT

Figure 1:
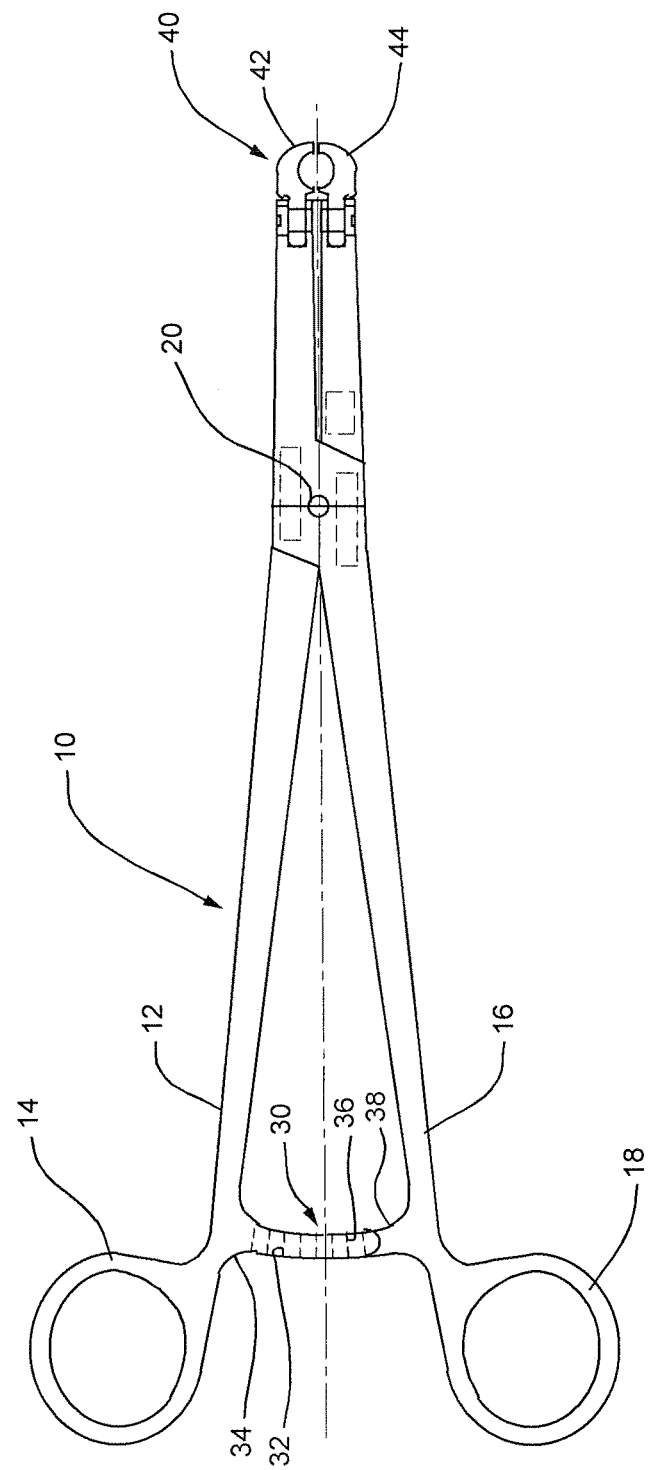
FIG. 1 is a schematic top plan view of an illustrative embodiment of the rod forceps of the present invention.

FIG. 1 is a schematic illustration of a top plan view of an illustrative embodiment of the rod forceps of the present invention. The rod forceps device 10 includes a handle member 12 with a generally circular opening 14 for insertion of the surgeon's finger. Similarly, handle member 16 has opening 18 for insertion of the thumb of the surgeon thus allowing the device 10 to be grasped and manipulated during a procedure.

The handle members 12 and 16 are coupled at a pin 20, such that each handle member rotates about the pin to thereby open and close the device 10. The handle members also include a mating ratchet locking arrangement 30 which can be adjusted and locked into a desired position once the device is suitably located. More specifically, the handle member 12 has a set of ratcheting teeth 32 disposed on an extension arm 34 and the handle member 16 has a set of cooperating ratcheting teeth 36 on its corresponding extension arm 38, thus forming the mating locking arrangement 30.

A pivoting jaw assembly 40 is located at a distal end of the instrument. The handle member 12 has a pivoting tip 44 and the handle member 16 has a pivoting tip 42. The jaw assembly 40 can be opened to insert a rod or other device to be used during a surgical procedure, and can then be closed around the rod to hold it in place while it is being positioned within the appropriate location in the surgical field.

FIG. 2 is a schematic side elevation of an illustrative embodiment of the rod forceps device 10 of the present invention. As shown in the side elevation of FIG. 2, the pivoting jaw assembly 40 is comprised of pivoting tip 44, and pivoting tip 42 (not visible in FIG. 2). The pivoting tip 44, for example is coupled to pin 50 in such a manner that is can be rotated about the pin 50 in the direction of the arrows X or Y.

FIG. 3 is a cross section of the pivoting jaw assembly 40 taken along lines A-A of FIG. 2. The pivoting tip 42 is coupled at a rotation assembly 52. In one embodiment of the invention, the rotation assembly 52 may be a simple pin allowing free rotation thereabout. In another embodiment of the invention, the rotation assembly can be comprised of a slotted screw 54 and a disc spring 56, which cooperate to allow the pivoting tip 42 to hold its position once it is set at a desired angle while in use. Similarly, the pivoting tip 44 is coupled at a pin, or with a rotation assembly 62 having a slotted screw 64 and disc spring 66 which cooperate to allow pivoting tip 44 to hold its position. It should be understood that there are many other types of mechanical arrangements that can be used to provide rotation and position locking functions to the pivoting jaw assembly 40.

The pivoting tip 42 has an inner contour 72 that is shaped to hold a surgical rod or other device. Similarly, the pivoting tip 44 has inner contour 74. Various embodiments of the device of the present invention can be machined with different contours and contours of different sizes, depending upon the intended application of the invention. The entire device 10 is illustratively constructed of stainless steel or other materials suitable for surgical applications.

It should be understood that the pivot tipped rod forceps of the present invention provide many advantages including providing a surgeon with better visibility and better leverage to apply force to an object. In addition, the invention has the particular advantage in that the rod may be aligned parallel with the basic instrument, allowing the rod to pass through a much smaller incision, or in some cases, the rod passes through tubes or port devices. Once through the facia, pressure may be exerted in a downward manner on the end of the rod, and the rotating tips allow the rod to pivot down into the seats of the pedicle screws already in place.

It should also be understood that the forgoing description has been directed to particular embodiments of the invention. It should be apparent, however, that other variations and modifications may be made to the described embodiments with the attainment of some or all of their advantages. Therefore, those skilled in the art should recognize that changes may be made in form and detail without departing from the spirit and scope of the invention.

What is claimed is:

1. A surgical forceps instrument for placing an object in a body portion during a surgical procedure, comprising:
    an instrument body having at least two handle members, each said handle member having a handle portion at a proximal end, and a working portion at a distal end;
    a connection assembly coupling together said handle members at a point between the proximal end and the distal end, and allowing for a rotation about said point of the handle members with respect to each other; and
    a pivoting jaw assembly disposed at the distal end of each handle member that in an open position allows the object to be inserted into the pivoting jaw assembly, and when closed allows the object to be held in the pivoting jaw assembly and then freely rotate to a desired angle with respect to the instrument body, the pivoting jaw assembly configured to hold the object substantially parallel to the instrument body for introduction of the object into the body portion, and configured to allow the object to freely rotate to the desired angle with respect to the instrument body during the surgical procedure.

2. The surgical forceps instrument as defined in claim 1 wherein said pivoting jaw assembly comprises a pivoting tip on each handle member.

3. The surgical forceps instrument as defined in claim 2 wherein said pivoting tip on each handle member has an inner contour that is shaped to hold said object.

4. The surgical forceps instrument as defined in claim 3 wherein said object to be held by said pivoting tip comprises a surgical rod, and said inner contour is sized to tightly engage an outer circumference of said surgical rod.

5. The surgical forceps instrument as defined in claim 2 wherein said pivoting jaw assembly comprises at the distal end of each handle member a rotation assembly having a pin allowing free rotation thereabout of said pivoting tip.

6. The surgical forceps instrument as defined in claim 2 wherein said pivoting jaw assembly comprises at the distal end of each handle member a rotation assembly having a slotted screw and a disc spring associated with each pivoting tip, which cooperate to allow each pivoting tip to hold a position once set at the desired angle with respect to the instrument body during the surgical procedure.

7. The surgical forceps instrument as defined in claim 2 wherein said pivoting jaw assembly comprises means for rotation and position locking of each said pivoting tip, which cooperate to allow each pivoting tip to hold a position once set at the desired angle with respect to the instrument body during the surgical procedure.

8. The surgical forceps instrument as defined in claim 1 wherein said surgical forceps instrument is substantially comprised of stainless steel.

9. The surgical forceps instrument as defined in claim 1 further comprising each handle member having an opening at a proximal end thereof adapted to receive a finger or thumb of a user of the surgical forceps instrument.

10. The surgical forceps instrument as defined in claim 9 further comprising each handle member having an extension arm disposed near said opening, said extension arm having a set of cooperating ratcheting teeth configured to form a mating locking arrangement when said surgical forceps instrument has engaged said object.

11. A surgical forceps instrument for placing a surgical rod in a body portion during a surgical procedure, comprising:
    an instrument body having at least two handle members, each handle member having a handle portion at a proximal end, and a working portion at a distal end;
    means for allowing rotation of the handle members with respect to each other, the means for allowing rotation disposed between the proximal end and the distal end of each handle member; and
    means for holding the object that are disposed at the distal end of each handle member, the means for holding the object configured to hold the object substantially parallel to the instrument body for introduction of the object into the body portion, and configured to allow the object to freely rotate to a desired angle with respect to the instrument body while being held by the means for holding the object during the surgical procedure.

12. The surgical forceps instrument as defined in claim 11 wherein the means for holding the object comprises a pivoting tip on each handle member.

13. The surgical forceps instrument as defined in claim 12 wherein the pivoting tip on each handle member has an inner contour that is shaped to hold the object.

14. The surgical forceps instrument as defined in claim 11 wherein the object is a surgical rod and the means for holding the object is sized to engage an outer circumference of the surgical rod.

15. The surgical forceps instrument as defined in claim 11 further comprising:
    means for rotation and position locking that cooperate to allow the means for holding to hold a position once set at the desired angle with respect to the instrument body during the surgical procedure.

16. A surgical forceps instrument for placing a surgical rod in a body portion during a surgical procedure, comprising:

an instrument body having at least two handle members, each handle member having a proximal end and a distal end;

a connection assembly coupling the two handle members to each other at a point between the proximal end and the distal end, the connection assembly allowing for rotation of the handle members with respect to each other; and a pivoting jaw assembly disposed at the distal end of each handle member, the pivoting jaw assembly including for each handle member:

a pivoting tip having an inner contour that is shaped to encage an outer circumference of the surgical rod, and a pin or screw coupling the pivoting tip to the distal end of the respective handle member, the pin or screw allowing for free rotation of the pivoting tip to a desired angle with respect to the respective handle member, wherein the pivoting jaw assembly is configured to hold the surgical rod substantially parallel to the instrument body for introduction of the surgical rod into the body portion, and configured to allow the surgical rod to freely rotate to a desired angle with respect to the instrument body after introduction into the body portion.

17. The surgical forceps instrument as defined in claim 16, wherein the pin or screw is a screw, and the pivoting jaw assembly includes for each handle member a disc spring that cooperates with the screw to hold the pivoting tip at the desired angle.

* * * * *